United States Patent [19]

McCartney

[11] 3,976,066
[45] Aug. 24, 1976

[54] SKIN PROTECTIVE DEVICE

[76] Inventor: James S. McCartney, 2645 S. 312th St., Federal Way, Wash. 98002

[22] Filed: Apr. 28, 1975

[21] Appl. No.: 572,275

[52] U.S. Cl. .............................. 128/153; 128/154
[51] Int. Cl.² ........................ A61F 5/30; A61F 13/00
[58] Field of Search .............. 128/132 R, 149, 82, 128/157, 154, 153

[56] References Cited
UNITED STATES PATENTS

| 695,761 | 3/1902 | Peacock | 128/154 |
| 3,503,392 | 3/1970 | Beeman | 128/132 R |

FOREIGN PATENTS OR APPLICATIONS

| 867,247 | 7/1941 | France | 128/154 |
| 8,600 | 1888 | United Kingdom | 128/154 |
| 406 | 1898 | United Kingdom | 128/154 |
| 288,220 | 7/1927 | United Kingdom | 128/154 |

*Primary Examiner*—Lawrence W. Trapp
*Attorney, Agent, or Firm*—Cole & Jensen

[57] ABSTRACT

A skin protective device, which includes one or more resiliently deformable mounting members capable of deforming to the contour of selected skin areas situated near the skin area to be protected. In use, the mounting members are secured to the selected skin areas. One or more substantially rigid protective elements, forming an air permeable protective barrier, are mounted on the mounting members so that the air permeable protective barrier extends over and is spaced away from, the skin area to be protected.

45 Claims, 29 Drawing Figures

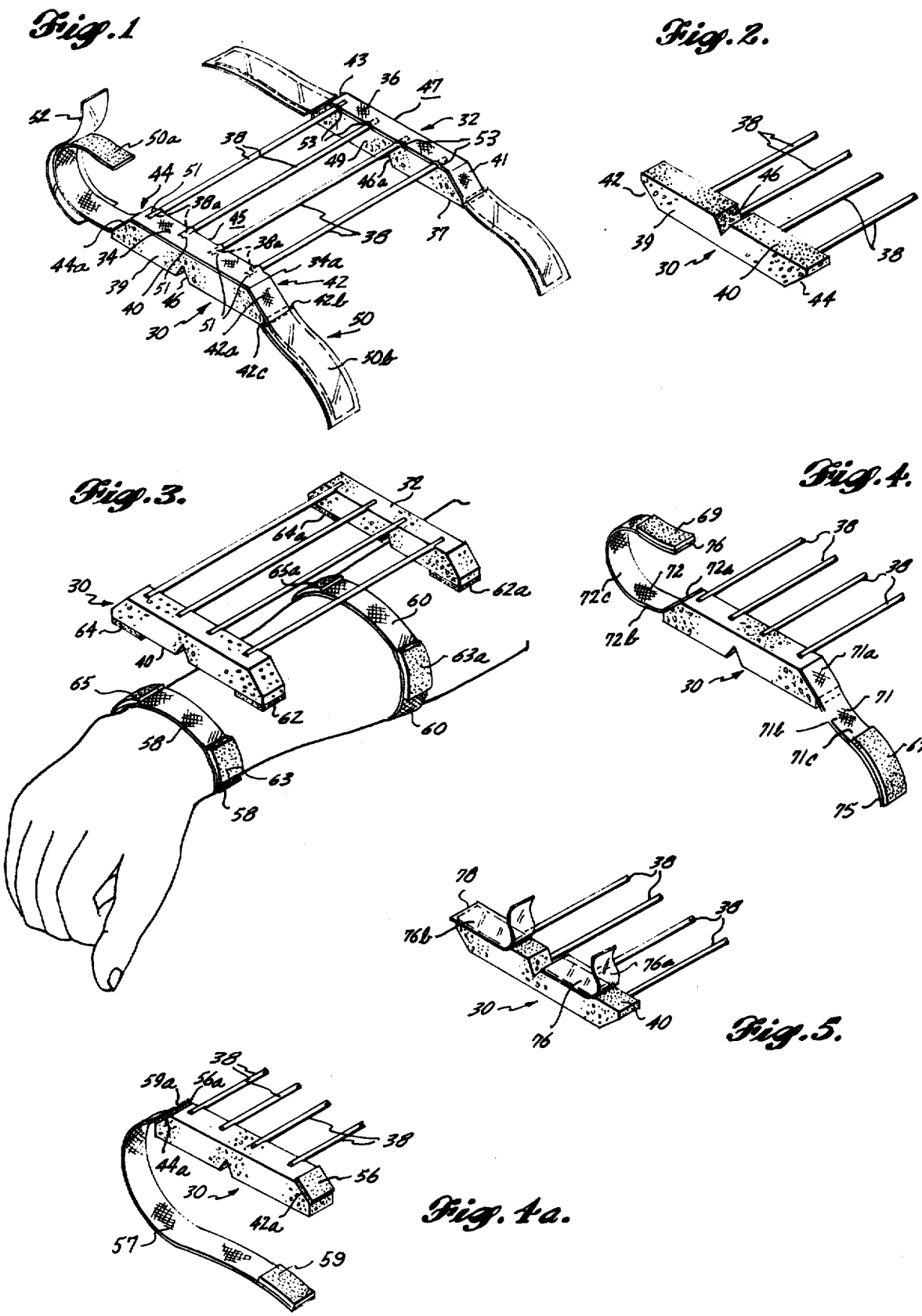

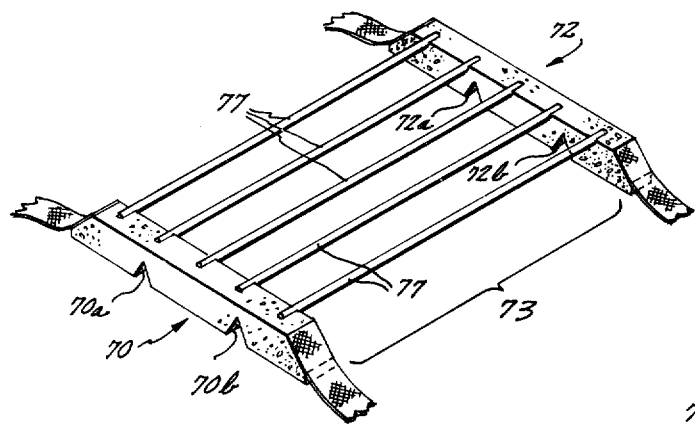
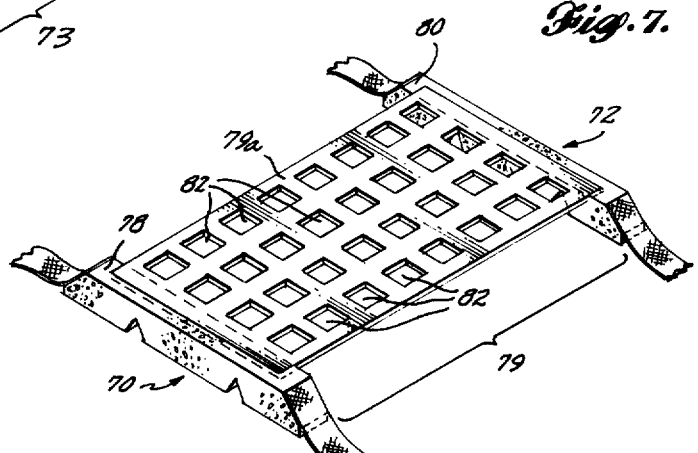
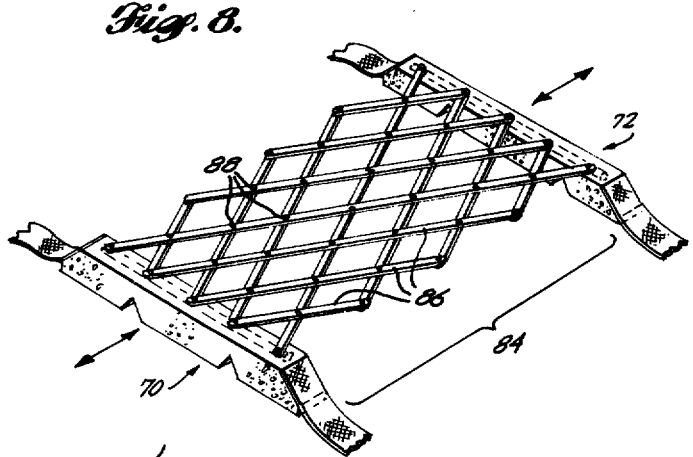
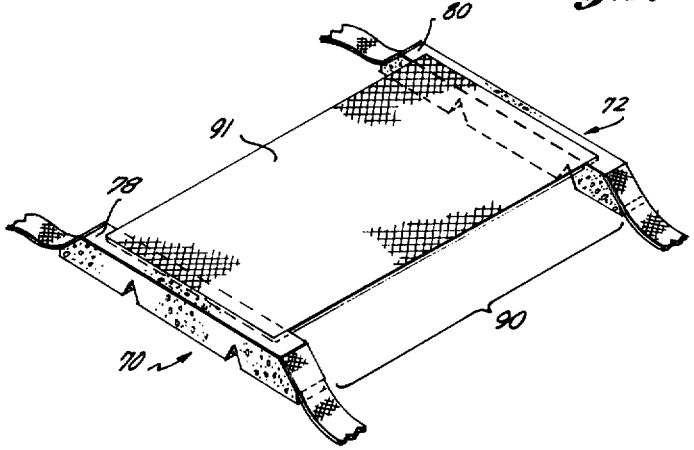
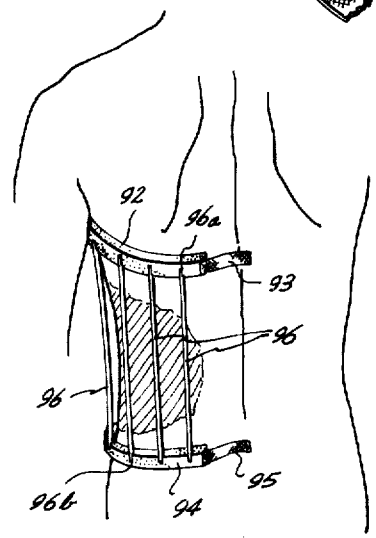

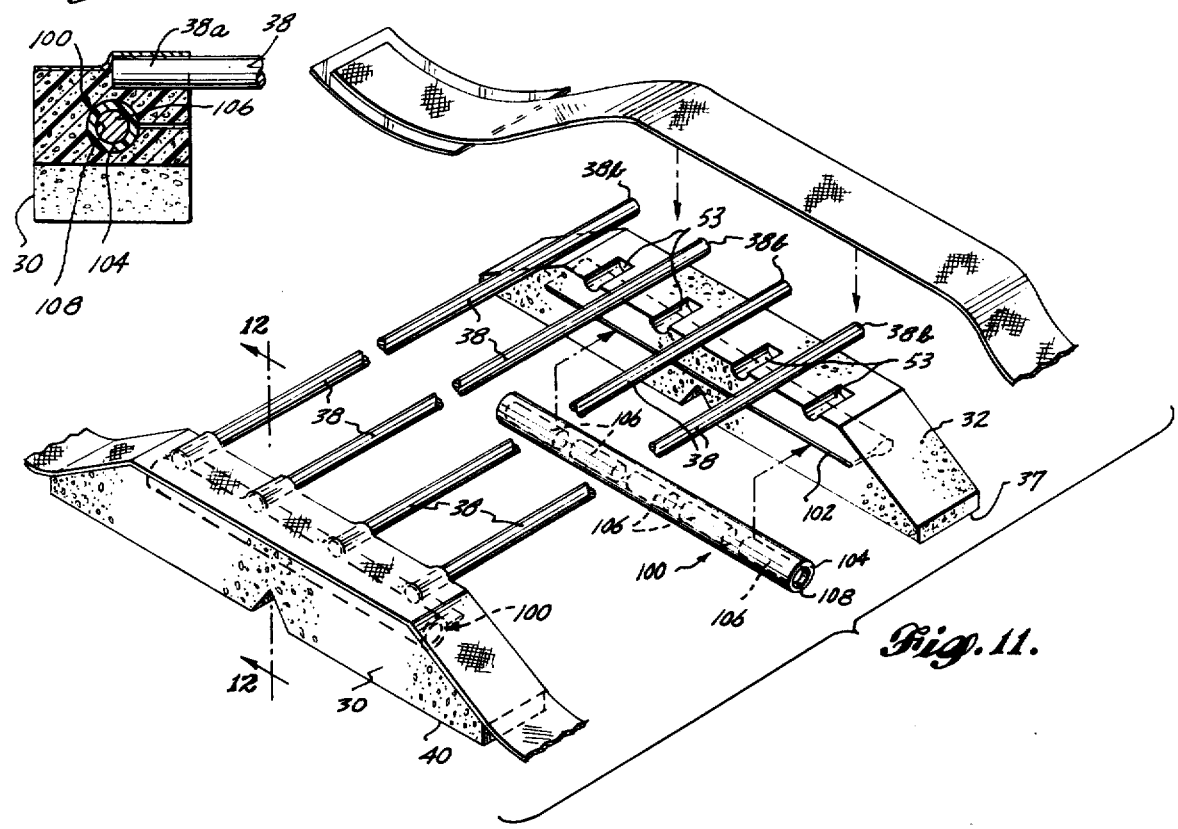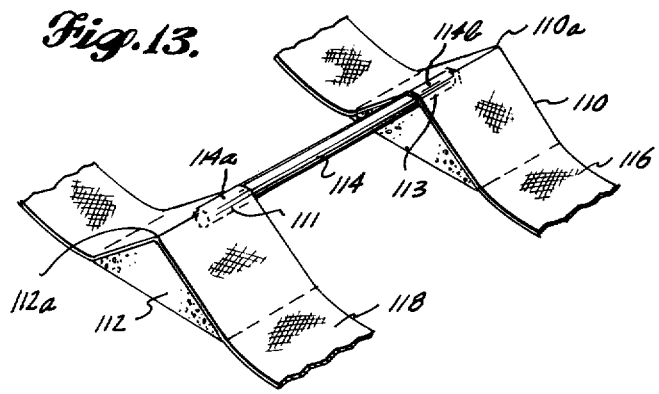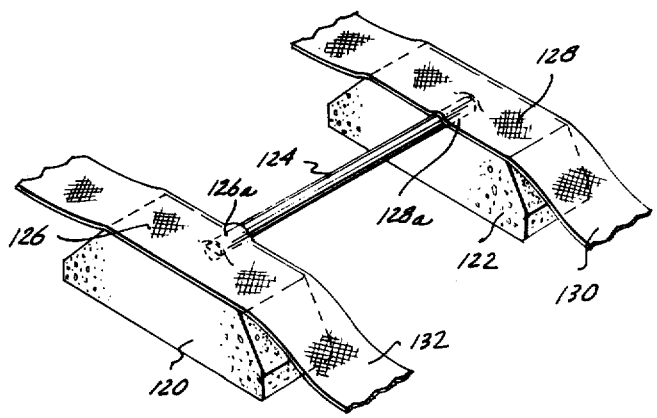

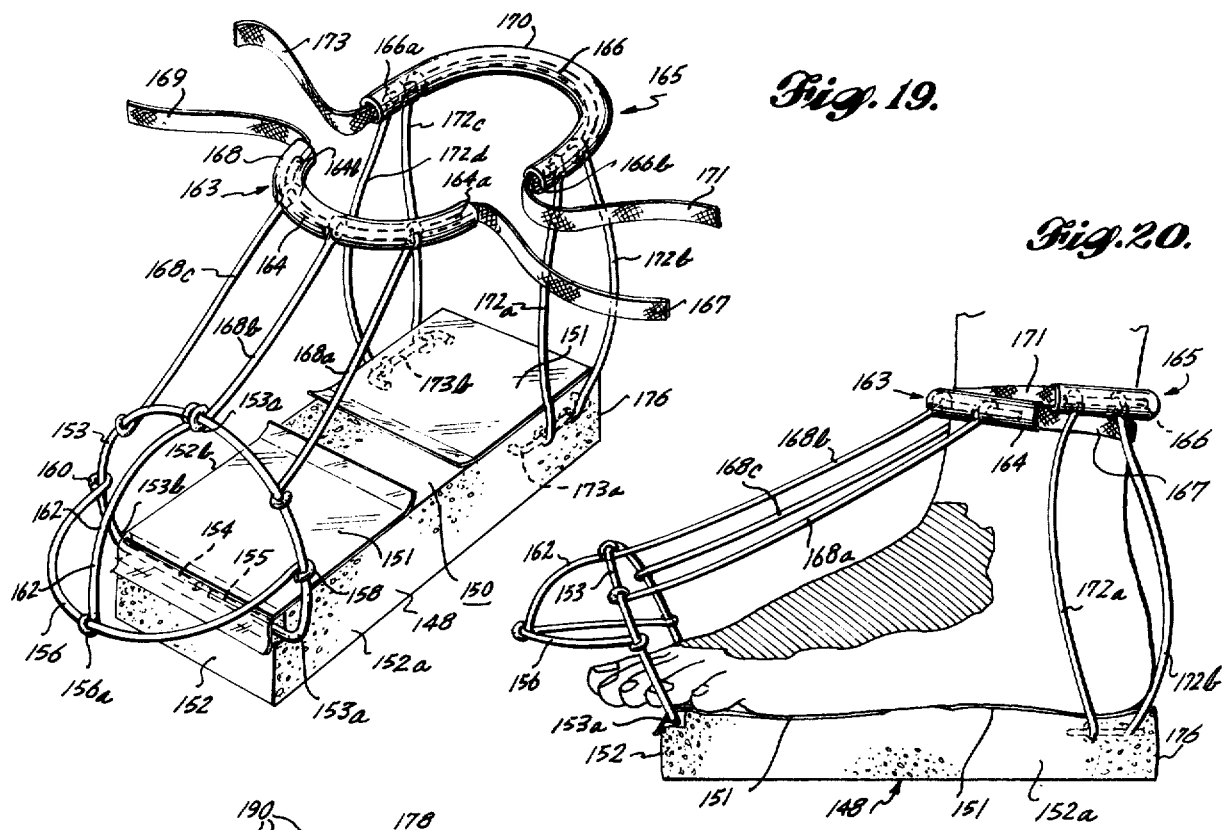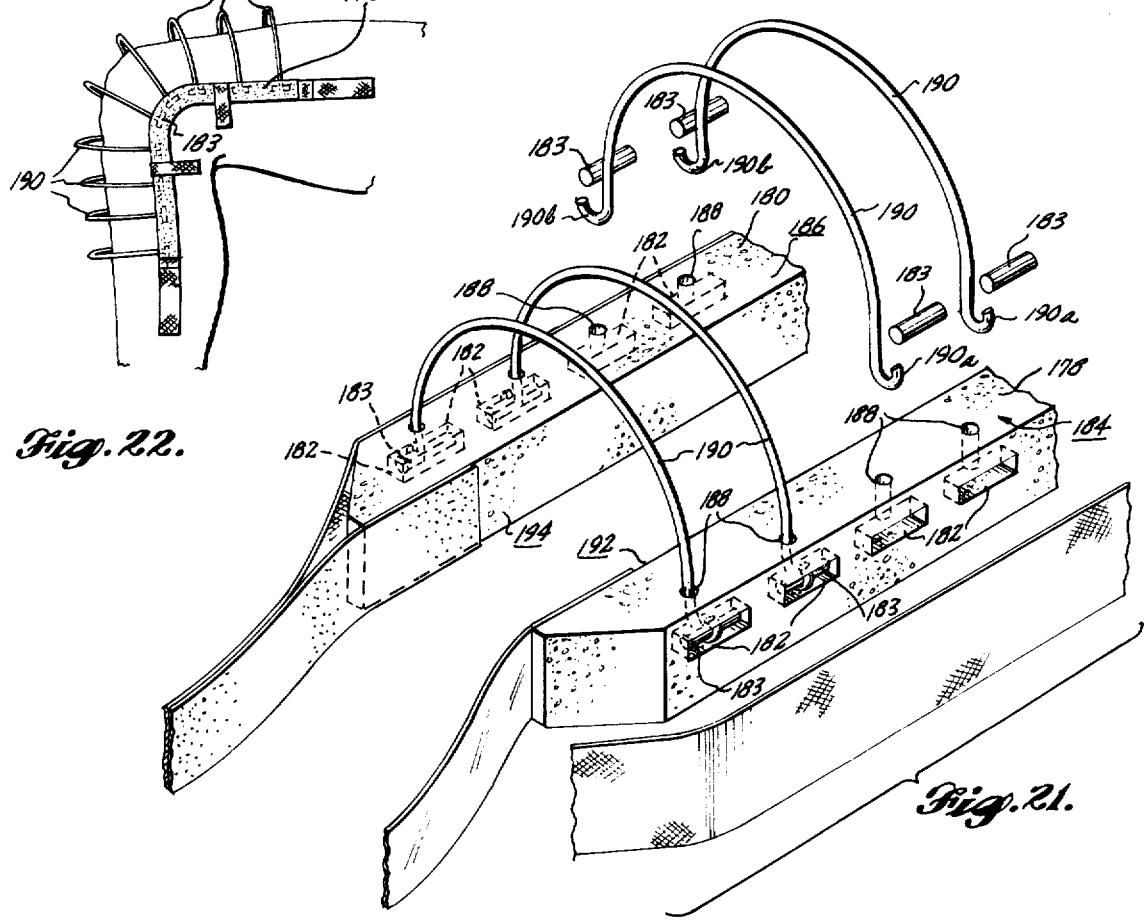

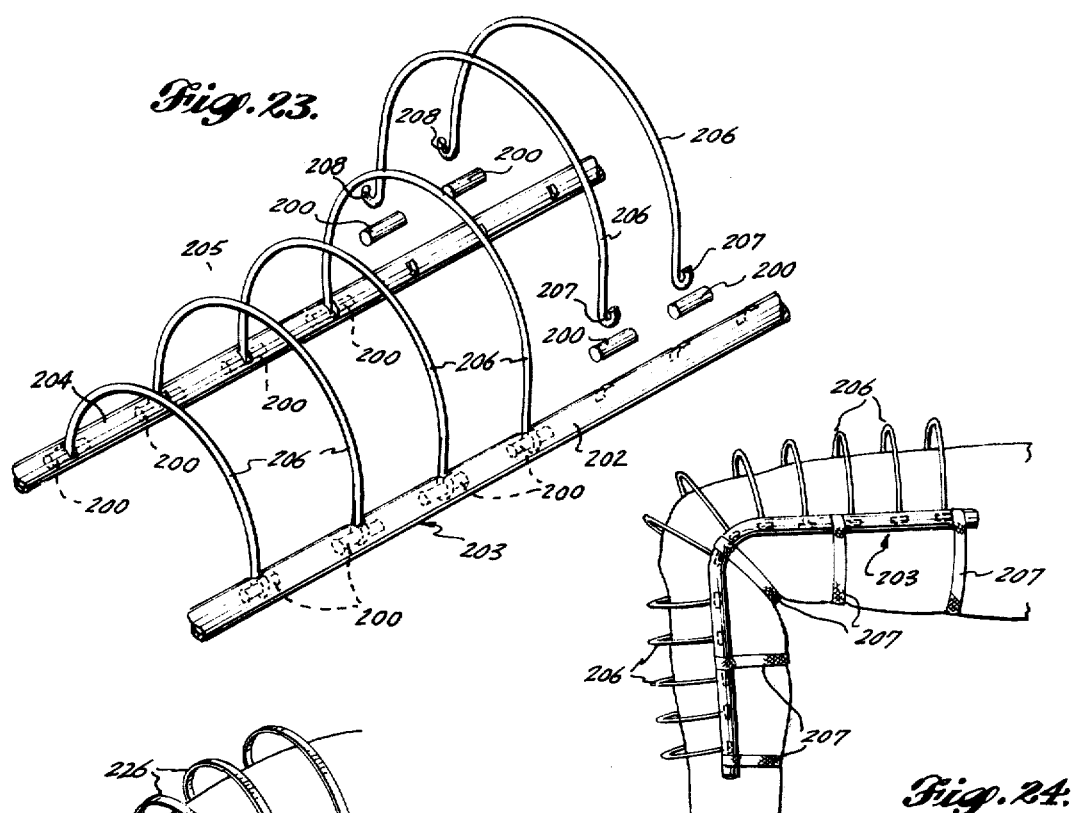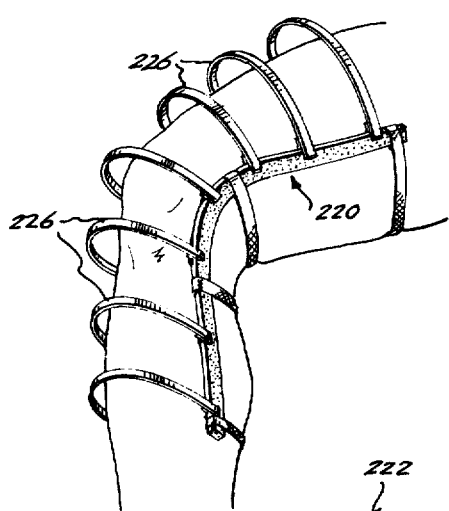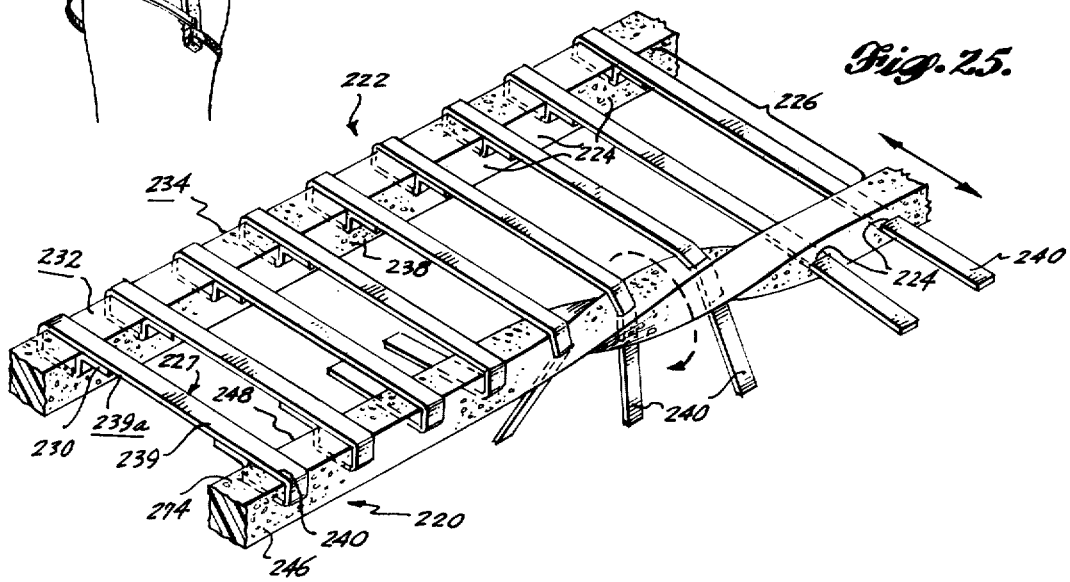

SKIN PROTECTIVE DEVICE

BACKGROUND OF THE INVENTION

This invention relates generally to the art of medical aids, and more specifically is concerned with protection of wounded or otherwise sensitive areas of the skin.

Small skin abrasions, including cuts, scrapes or other minor skin wounds, are conventionally protected from contact with clothing, dirt, and other foreign articles by well-known adhesive bandages or gauze. However, in the case of serious wounds to the skin, such as caused by a severe burn, surgical incision, skin graft, or the like, conventional bandages or gauze dressings are of relatively little aid in healing, particularly where the wound is of a relatively large size. Typically, such a wound requires not only a significant amount of protection from contact with foreign articles, such as clothing, bed linen, etc., but requires a free circulation of air and an unrestricted blood supply for fast and effective healing. The size of the affected skin area along often presents a substantial impediment to proper healing, as it is difficult to maintain a large wound or burn substantially free from contact with foreign articles.

Surgical wound protectors have been developed which provide a degree of protection for certain types of skin wounds such as severe cuts or surgical incisions. However, these devices have several disadvantages even when used with such wounds, and furthermore are not suitable for other types of skin wounds, such as burns or skin grafts. A significant disadvantage of such known surgical wound protectors is their inability to conform to the natural outline of the body, a disadvantage which is particularly troublesome when the skin wound is on a highly contoured portion of the body. Additionally, and perhaps even more importantly, the use of such surgical wound protectors to protect incisions result in a substantial amount of pressure on the skin area adjacent the sensitive wound area, resulting in a reduction of the blood supply to the affected skin area, and possibly causing damage to both the wounded skin area and the surrounding skin area.

In view of the above, it is a general object of the present invention to provide a skin protective device which overcomes the disadvantages of the prior art discussed above.

It is another object of the present invention to provide such a protective device which is capable of protecting relatively large areas of the skin from contact with foreign articles.

It is a further object of the present invention to provide such a protective device which permits the air to freely circulate about a wounded or sensitive skin area.

It is another object of the present invention to provide such a protective device which is conformable to the contour of the portion of the body near or adjacent the wounded skin area.

It is a still further object of the present invention to provide such a skin protective device which minimizes restriction of blood flow to the area of the skin wound, or surrounding area.

It it yet another object of the present invention to provide such a protective device which is adjustable in size to fit over the area of the skin wound.

It is another object of the present invention to provide such a protective device which may be conveniently adhered to the skin area in the vicinity of the skin wound, and which will flex with the body in the natural movement thereof.

It is a further object of the present invention to provide such a protective device which permits access to and inspection of the wounded skin area without removing or otherwise disturbing that portion of the skin protective device adhered to the near or adjecent skin areas.

Various other objects and advantages will appear from the following description of several embodiments of the invention, and the novel features will be particularly pointed out hereafter in connection with the appended claims.

SUMMARY OF THE INVENTION

Accordingly, for protection of a first skin area of the body of a user, the present invention includes a resiliently deformable mounting means, which is positionable on a user's second skin area situated relatively near the first skin area, with the mounting means in use conforming to the contour of the second skin area when it is positioned thereon. Means are provided for securing the mounting means to the second skin area and to maintain it in a conforming relationship therewith, and protector means is provided which is at least semi-rigid and mounted on said mounting means, for preventing foreign articles from contacting said first skin area, said protector means being mounted so that it extends over and is spaced away from the first skin area so as to protect the first skin area from contact. The mounting means is furthermore sufficiently elastic that the contact between the mounting means and the second skin area is not altered during flexure of the second skin area, caused by, for instance, movement of the body.

DESCRIPTION OF THE DRAWINGS

A more thorough understanding of the invention may be obtained by a study of the following detailed description taken in connection with the accompanying drawings in which:

FIG. 1 is an isometric view of one embodiment of the skin protective device of the present invention, showing a first variation of the means maintaining the skin protective device on a user.

FIG. 2 is an isometric view of a skin protective device similar to that of FIG. 1 but illustrating a second variation of the means securing and maintaining the skin protective device on the user.

FIG. 3 is an isometric view of a skin protective device similar to that of FIG. 1, but illustrating a third variation of the means secured and maintaining the skin protective device on the user. FIG. 4 is an isometric view of a skin protective device similar to those of FIGS. 1 through 3, but illustrating a fourth variation of the means securing and maintaining the skin protective device on the user.

FIG. 4a is an isometric view showing an embodiment similar to those of FIGS. 1 through 4, but illustrating a fifth variation of the means securing and maintaining the skin protective device on the user.

FIG. 5 is an isometric view of a skin protective device similar to those of FIGS. 1 through 4, but illustrating a sixth variation of the means securing and maintaining the skin protective device on the user.

FIG. 6 is an isometric view of one embodiment of the skin protective device of the present invention showing a first type of protective member.

FIG. 7 is an isometric view of a skin protective device similar to that of FIG. 6, showing a second type of protective member.

FIG. 8 is an isometric view of a skin protective device similar to that of FIGS. 6 and 7, showing a third type of protective member.

FIG. 9 is an isometric view of a skin protective device similar to that shown in FIGS. 5 through 8, showing a fourth type of protective member.

FIG. 10 is a view showing the skin protective device of the present invention in position on the side and back of a user.

FIG. 11 is an isometric view of a heavy duty embodiment of the skin protective device of the present invention.

FIG. 12 is a cross-sectional view taken along lines 12—12 in FIG. 11.

FIG. 13 is an isometric view showing a first variation of a single pin embodiment of the skin protective device of the present invention.

FIG. 14 is an isometric view showing a second variation of a single pin embodiment of the skin protective device of the present invention.

FIG. 19 is an isometric view of another embodiment of the skin protective device of the present invention, adapted particularly for use in protecting human feet.

FIG. 20 is a side elevational view showing the device of FIG. 19 in position on a human foot.

FIG. 21 is a partially exploded isometric view showing another embodiment of the skin protective device of the present invention, particularly adapted to use around the limb joints of a user.

FIG. 22 is a side elevational view showing the device of FIG. 21 in position on a human leg.

FIG. 23 is a partially exploded isometric view showing another embodiment of the skin protective device of the present invention, particularly adapted for use around the limb joints of a user.

FIG. 24 is a side elevation view showing the device of FIG. 23 in position on a human leg.

FIG. 25 is an isometric view showing another embodiment of the skin protective device of the present invention which is particularly adapted to be adjustable to cover various size wounds, particularly around limb joints of a user.

FIG. 26 is a side view showing the device of FIG. 25 in position on a human leg.

FIG. 28 is an isometric view showing an embodiment of the skin protective device of the present invention wherein the protector means is removable.

DESCRIPTION OF THE PREFERRED EMBODIMENT

Figure 15:
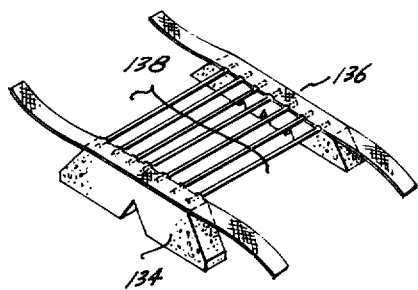
FIG. 15 is an isometric view showing another embodiment of the skin protective device of the present invention, adapted particularly for use on the hands and feet of a human user.

Referring to FIG. 1, one embodiment of the skin protective device of the present invention includes two elongated mounting pads 30 and 32 which are spaced apart but connected to each other by a plurality of rigid or at least semi-rigid rod-like protective elements 38 which are spaced sufficiently apart from one another to permit a free movement of air therebetween, and between the mounting pads 30 and 32. Mounting pads 30 and 32 are sufficiently deformable so that they are capable of substantially conforming to the outline of the skin area of the body in the vicinity of the skin wound area, and are also sufficiently resilient and elastic so that the entire protective device can move or flex with the natural movement of the body without altering the contact between the mounting pads and the second skin area, and so that upon removal of the mounting pads 30 and 32 from the body, they return substantially to their original shape. Such a structure prevents changes in pressure on the second skin area, causing restriction of blood flow to the first skin area, while permitting movement of the semi-rigid protector means with the natural flexure of the body. Thus, the mounting pads in effect take up the movement of the protector means without disturbing the established contact between the mounting pads and the second skin area. Although various materials having these characteristics can be used for the mounting pads it has been found that a particular type of foam rubber, generically referred to as poly-ether urethane foam, will work well.

Although the dimensions of each moutning pad shown in FIG. 1 will necessarily vary depending upon the size and position of the wound, mounting pads 30 and 32 shown in FIG. 1 are approximately 1 inch by 1 inch in cross-sectional outline, and their length will vary from approximately 2 inches to over a foot depending upon the particular application. Furthermore, the structure of FIG. 1 can be provided in rolls several feet in length, portions of which can be selectively removed as the need arises, with each portion cut to precisely the desired length. Mounting pad 30 has an upper surface 34 in which first ends 38a the protective elements 38 are embedded, a lower surface 40 and two end surfaces 42 and 44. Mounting pad 32 is substantially identical to mounting pads 30 and has an upper surface 36, a lower surface 37, and two end surfaces 41 and 43. Defined in the lower surfaces 40 and 37 of mounting pads 30 and 32 in some embodiments of the skin protective device is at least one notch. Referring to mounting pad 30, for example, triangular-shaped notch 46 is oriented such that its apex is nearest upper surface 34 of mounting pad 30, and such that it extends through mounting pad 30, i.e., from exterior side 39 to interior side 45. Mounting pad 32 has an identical notch 46a defined therein, which notch extends between exterior side 47 and interior side 49 thereof. The purpose of notches 46 and 46a is to provide a space within the volume of the mounting pads to permit easy and convenient deformation of the mounting pads, and to minimize or prevent wrinkling or bulging thereof.

In several embodiments of the present invention, the end surfaces of the mounting pads, e.g., end surfaces 42 and 44 of mounting pad 30, are angled to minimize concentrated pressure an the wounded and surrounding skin areas and to insure stability of the protective device when secured to the body, especially when surgical or other adhesive tape is used to secure the mounting pads to the skin. Referring, for instance, to FIG. 1, end surface 42 of mounting pad 30 includes an inclined surface portion 42a which tapers downwardly and outwardly towards lower surface 40 from one end 34a of upper surface 34. The angle of incline of inclined surface portion 42a may vary substantially and is provided primarily to minimize pressure and insure vertical stability of mounting pad 30 when it is secured to the body. An angle of 45° has been found to work well. At some defined point 42b along end surface 42, inclined surface portion 42a terminates, and a blunt surface portion 42c begins, blunt surface portion 42c rising substantially perpendicularly from lower surface 40 to intersect inclined surface portion 42a. Blunt surface portion 42c has been found to be a convenient configuration for purposes of securing the mounting pads to the body and preventing erosion, i.e. partial disintegration, of the tip of end surface 42 caused by relative movement between the protective device and the body. It should be understood that each end surface of mounting pads 30 and 32 has the same configuration as end surface 42 described in detail with respect to mounting pad 30.

Extending between mounting pads 30 and 32, which in use are positioned on opposing sides of the skin wound, is a protector means in the form of protective elements 38, opposing ends of which are embedded in top surfaces 34 and 36 of mounting pads 30 and 32. FIG. 1 discloses the use of four protective elements 38 spaced parallel with, and apart from, each other. A plurality of spaced groves 51 and 53 are defined in the upper surface of the mounting pads and extend from their interior sides toward their exterior sides. Although the embodiment shown in FIG. 1 and several other embodiments show grooves in the upper surfaces of the mounting pads to receive the protective elements, other structural configurations can be used to secure the protective elements to the mounting means. For instance, the respective ends of protective elements 38 may be completely embedded in mounting pads 30 and 32. Protective elements 38, which in one embodiment take the form of ¼ inch bars, such as wooden dowels, are then positioned such that their respective ends lie in grooves 51 in mounting pad 30 and in grooves 53 in mounting pad 32. Protective elements 38 are then secured in grooves 51 and 53 by a flexible adhesive. Protective elements 38 then extend over and are spaced away from the skin wound area. Protective elements 38 are preferably at least semi-rigid, sufficient to withstand minimal force in the direction of the wound without deforming and are spaced away from the wound area by the mounting pads on which they are mounted, on the order of ½ inch to 1 inch in the embodiment of FIG. 1. Such an arrangement provides a free flow of air around the wound and permits natural healing to take place while protecting the wound from contact with clothing, bed linen, and other foreign articles.

In use, mounting pads 30 and 32 are deformed to and secured to the skin area relatively near and typically immediately adjacent the wounded skin area. Many different means of securing and maintaining mounting pads 30 and 32 to the skin are acceptable, as will be hereinafter clarified. Although each mounting pad has its own securing and maintaining means, the variations thereof will, for purposes of clarity, be explained with respect to just one mounting pad. FIG. 1 shows a strip of surgical adhesive tape 50 which extends the length of upper surface 34 and opposing inclined surface portions 42a and 44a of mounting pad 30, portions 50a, 50b of tape strip 50 extending therebeyond a sufficient distance to provide a secure adhesive contact between mounting pad 30 and the skin area to which it is applied. Mounting pad 30 is thus first deformed to the contour of the skin area adjacent the wounded area, tape shield 52 is then removed from portions 50a and 50b of tape strip 50, and portions 50a and 50b are then secured to the user's skin in the vicinity of the wounded skin area. In the embodiment of FIG. 1, tape strip 50 runs along the length of, and is secured to, the upper surface 34 of mounting pad 30. This configuration acts to assist in maintaining the protective elements 38 in grooves 51.

Besides using the means of surgical adhesive tape to secure and maintain mounting pads 30 and 32 to the skin as shown in FIG. 1, other means can be used with considerable success. It is important, however, that the selected means, when applied, cause only a minimum amount of pressure or irritation to the skin area to which it is applied, so as to minimize the interference with the natural flow of blood into the skin area affected. Various adhesive means have been found to be effective by the inventor. FIG. 2 shows a portion of the protective device of FIG. 1 wherein the lower surface 40 of mounting pad 30 is coated with a adhesive, with the mounting pad 30 then being positioned on, or secured directly to the skin of the user adjacent the wound area. The adhesive maintains the mounting pads securely on the skin.

FIG. 3 shows a skin protective device similar to that shown in FIG. 1, with the addition of bands 58 and 60 positioned on or around the arm of a user. Each band 58, 60 have tabs 63, 65, and 63a, 65a secured to them at spaced positions therealong. Secured to the lower surface 40 of mounting pad 30 are tabs 62 and 64, spaced to match the distance between tabs 63, 65 on band 58. Tabs 52, 63, 64, 65 are of a special material which, when pressed together, adhere to each other, such as, for instance, the material sold under the trademark VELCRO. Tabs 63a and 65a on band 60 function similarly with matching tabs 62a and 64a on mounting pad 32. Such a means is particularly useful when a skin area on a small diameter portion of the body, such as an arm or a leg, is to be protected. In such an application, bands 58 and 60 are wrapped around the arm or leg to be protected. Mounting pads 30 and 32 with the protective elements 38 extending therebetween may thus be conveniently removed for treatment and inspection of the wound without in any way disturbing the wounded skin area or the skin area immediately thereadjacent.

Another variation of the securing and maintaining means is shown in FIG. 4, in which tabs 67 and 69 are attached to strips 71, 72 of flexible material, portions 71a and 72a of which in turn are attached to the mounting pad 30. Tabs 67 and 69 are again a material similar to that sold under the trademark VELCRO. Strip 71 has a lower surface 71b, and an upper surface 71c, and tab 67 is attached to upper surface 71c near the outer end thereof, while tab 69 is attached to strip 72 near the outer end 76 thereof on lower surface 72b. A variation of the embodiment of FIGS. 3 and 4 is shown in FIG. 4a. Mounting pad 30 is provided with tabs 56 and 56a on the inclined surface portions 42a and 44a, respectively, of end surfaces 42 and 44. A flexible strip 71 is provided with tabs 59 and 59a at opposite ends thereof, or alternatively, tabs 59 and 59a may be one tab running the entire length of the flexible strip 71. Again, tabs 56, 56a and 59, 59a are made from a material having similar characteristics to that material sold under the trademark VELCRO. In use, the pressure of the mounting pad 30 against the skin of a user may be adjusted by varying the relative position of attachment between tabs 56 and 59, and between material tabs 56a and 59a. Another variation is shown in FIG. 5, in which double-backed adhesive tape is used. One side 76a of a strip 76 of double-backed adhesive tape attaches directly to lower surface 40 of mounting pad 30, while the other side 76b of strip 76 may be attached directly to the skin of the user. A tape shield 78 conveniently protects side 76b until the device is ready for use.

FIGS. 6 through 9 show skin protective devices having the same general characteristics as that shown in FIG. 1, with various forms of protector means extending between exemplary mounting pads 70 and 72. The protector means 73 of FIG. 6 includes a plurality of rod-like elements 77, which can be made from wood, fiberglass, or other substantially rigid material, similar to that shown in FIG. 1, except that five bars are provided in the embodiment shown in FIG. 6. Additionally in the embodiment of FIG. 6, two lower surface notches 70a, 70b, and 72a, 72b are defined in mounting pads 70 and 72. The number of dowels and the number of lower surface notches depends upon the size of the skin area to be protected. Although the protector means shown in FIG. 6 and several of the other embodiments is substantially rigid, the protector means is secured to the mounting pads 70 and 72 with a rubberized adhesive, which, in combination with the resilient characteristics of the mounting pad permits relative movement and flex of the protective device without causing undue tension on the wound area or causing the device itself to break up.

FIG. 7 shows mounting pads 70 and 72, similar to that shown in FIG. 6, but illustrates a protector means 79 in the form of a grid-like sheet 79a which extends between mounting pads 70 and 72, and which has a width substantially equal to the length of upper surfaces 78, 80 of mounting pads 70 and 72. Defined in the sheet 79a are a plurality of openings 82, which preferably are spaced along the length and breadth of sheet 79a. The openings 82 are preferably regularly spaced and are on the order of 1/6 inch to 1 inch sq. and are sufficient in quantity to permit a substantial amount of air to flow through the sheet 79a and around the wounded skin area. In the protector means embodiment illustrated in FIG. 7, the openings 82 in sheet 79a take the form of a square and are arranged in rows and files to cover the entire surface area of sheet 79a. Other arrangements of sizes of openings can be used with equal success.

FIG. 8 shows another type of grid used as a protector means 84, extending between mounting pads 70 and 72. Protector means 84 has a scissors-like structural arrangement which comprises a plurality of rigid bars 86 of varying length, with bars 86 overlaying each other between mounting pads 70 and 72 so as to form diamond-shaped openings between bars 86. Bars 86 are connected to each other as well as mounting pads 70 and 72 by pin connections 88, which permit limited rotational movement of bars 86 relative to each other. When protector means 84 is secured between mounting pads 70 and 72, the relative movement of bars 86 permitted by pin connections 88 will permit the mounting pads 70 and 72 a range of movement toward and away from each other.

FIG. 9 shows another type of protector means 90 useful in the present invention, protector means 90 being a solid sheet 91 of material which is mounted between mounting pads 70 and 72 and which has a width sufficient to extend along a substantial portion of the upper surfaces 78 and 80 of mounting pads 70 and 72. Sheet 91 may in some cases be air permeable, to aid the free circulation of air about the wound area, and additionally may be flexible so as to aid in permitting natural movement of the body.

The protector means portion of the skin protective device can also be made removable, as shown in FIG. 28, so that the wound can be treated or inspected without the necessity of removing or otherwise disturbing the mounting means already in position and secured to the skin area adjacent the wound. Referring to FIG. 28, mounting pad 81 is slit lengthwise into top and bottom portions 81a and 81b, just beneath the point of attachment between protective elements 83 and mounting pad 81. Secured to the top surface 85 of bottom portion 81 and bottom surface 87 of top portion 81b, respectively, are tabs 89a, 89b, which adhere to one another when pressed together, such as the material sold under the trademark VELCRO. Such a structure retains its elastic, deformable characteristics, yet permits the protector means portion of the skin protective device to be conveniently removed to permit inspection and/or treatment of the wounded skin area.

FIG. 10 shows a skin protective device made according to the principles of the present invention in place on the body of a human, protecting a portion of the side and back area. Mounting pads 92 and 94 have been deformed to the contour of the body in the vicinity of the wound, and are shown to be located above and below the wound area, and in the embodiment of FIG. 10 are secured to the body by means of adhesive tape strips 93, 95. Protective elements 96, which are secured at opposite ends 96a, 96b thereof to mounting pads 92 and 94, extend over the wound area and protect it from contact with foreign articles. The protective elements 96 are secured to the mounting pads 92, 94 by a flexible adhesive and, if desired, covered with adhesive tape, so that they can move and flex with the natural movement of the body without coming loose from the mounting pads 92 and 94.

Referring now to FIGS. 11 and 12, a heavy duty type skin protective device is shown, adapted for use in circumstances where heavy pressure on the protector means is likely. The device shown in FIGS. 11 and 12 is similar in general configuration to the skin protective devices shown and described previously, in particular that of FIG. 1, but includes an elongated support element 100 which is embedded in a slot 102 defined within each of the mounting pads 30 and 32 along the respective lengths thereof, with slot 102, for instance, being located in mounting pad 32 intermediate of the grooves 53 in which ends 38b of protective elements 38 are positioned and the lower surface 37 of mounting pad 32.

The purpose of support element 100 is to maintain stand-off protective elements 38 from the wound when a significant amount of weight or other pressure is applied to the protective elements 38 in the direction of the wound, in order that the protective elements 38 do not themselves contact the wound. Such a heavy duty skin protective device would be useful, for instance, when the wound is in the area of the buttocks, and would permit the user to conveniently sit or lie down. Support element 100 may, of course, take various configurations within the spirit of the invention. For instance, support element 100 may be a solid section of flexible, but substantially nondeformable rubber, having various cross-sectional outlines, depending on the application. Other configurations and materials will naturally occur to one skilled in the art.

Support element 100 in the embodiment shown in FIGS. 11 and 12, however, comprises a flexible cylindrical tube 104, in which are inserted cylindrical lengths 106 of a nondeformable material having an outer boundary which mates with inner wall 108 of tube 104. Lengths 106 are spaced apart longitudinally along the length of tube 104, and are oriented in tube 104 such that one length 106 is directly beneath each end 38b of protective elements 38 in each mounting pad 30 and 32. The space in tube 104 between successive lengths 106 positioned therein permits flexibility and deformability of support element 100 and hence, mounting pads 30 and 32. Lengths 106 provide the required nondeformable support between the lower surface 40 and 37 of mounting pads 30 and 32 and protective elements 38 and hence prevent contact between protective elements 38 and the wound when significant pressure is applied to the protective elements 38.

Referring now to FIGS. 13 and 14, other embodiments of the skin protective device of the present invention are shown, which embodiments are similar to that shown previously, but which are designed to protect thin or small cuts and burns, and which can be used to compliment or replace bandaids. FIG. 13 shows two triangle-shaped mounting pads 110 and 112 with a single protective element 114 secured thereto and extending therebetween, with protective element 114 being in the form of a bar such as a ⅛ inch wooden dowel in the embodiment shown in FIG. 13. Protective element 114 has opposing ends 114a and 114b which are secured, respectively, to apexes 110a and 112a of mounting pads 110 and 112. Grooves 111 and 113 are provided in each apex 110a and 112a to receive ends 114a and 114b, respectively, of protective element 114. Adhesive strips 116 and 118 are provided with each mounting pad 110 and 112 to secure and maintain them in conformable contact to the body of a user in a manner similar to that shown in FIG. 1. The other securing and maintaining means of FIGS. 2–5 can, of course, also be used.

FIG. 14 discloses a variation of the embodiment of FIG. 13, having somewhat differently shaped mounting pads 120 and 122. As is the case with the device of FIG. 13, however, the device of FIG. 14 has but a single protective element 124. Mounting pads 120, 122 each have an outline which is substantially identical to that of mounting pads 30, 32 of FIG. 1, except that the length of mounting pads 120, 122 is on the order of 1 inch to 1 ½ inch. Protective element 124 extends between and is secured to mounting pads 120 and 122, respectively, substantially at the longitudinal midpoints 126a, 128a of upper surfaces 126 and 128 thereof. Securing and maintaining means 130 and 132, e.g. adhesive tape, are provided with each mounting pad 120 and 122 in a manner similar to that shown in FIG. 1, or in FIGS. 2–5, for maintaining mounting pads 120 and 122 in conforming contact with the body of a user.

Figure 16:
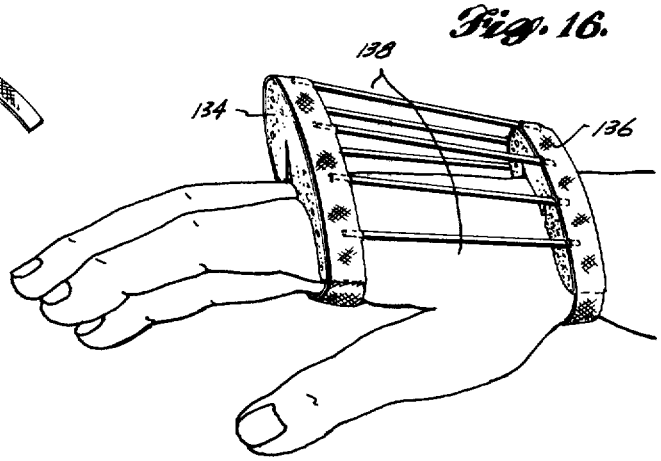
FIG. 16 is a elevational view showing the skin protective device of FIG. 15 in position on a human hand.

FIGS. 15 and 16 disclose another embodiment of the skin protective device of the present invention, which embodiment is particularly adapted for use on specialized areas of the body such as the human hand or the human foot. The principle structural distinction between the embodiments of FIGS. 15 and 16 and the embodiment of FIG. 1, is that one of the mounting pads, for instance mounting pad 134, has a greater depth, for instance 1 inch, and typically a greater length than the other mounting pad 136, which is approximately ½ inch deep. Otherwise, the embodiment of FIGS. 15 and 16 is structurally similar to that shown in FIG. 1, including two mounting pads, preferably made from a resiliently deformable material such as foam rubber, protector means extending between and secured to the mounting pads, such as the bars shown in FIGS. 15 and 16, and securing means for securing the mounting pads to the skin of a user, such as by surgical adhesive tape, as shown in FIGS. 15 and 16. When the device of FIG. 15 is applied to, for instance, a human hand, the shallower mounting pad 136 is positioned over a major joint, such as the wrist, while the deeper mounting pad 134 is then positioned at some selected point over the knuckles of the fingers. The variance in depth between mounting pads 134 and 136 is necessitated by the substantial amount of lateral (up-down) movement naturally occurring in the foot and wrist joints of a human during normal activity. If the depth of mounting pads 134 and 136 were maintained equal, the protective element 138, if rigid, would likely contact the wound upon ordinary movement of the hand and wrist or foot and ankle of the user. The greater depth of the one mounting pad 134 adjacent the extremities of the digits permits a substantial movement of the hand and ankle or foot and wrist without contact between the protective element 138 and the wound.

Figure 17:
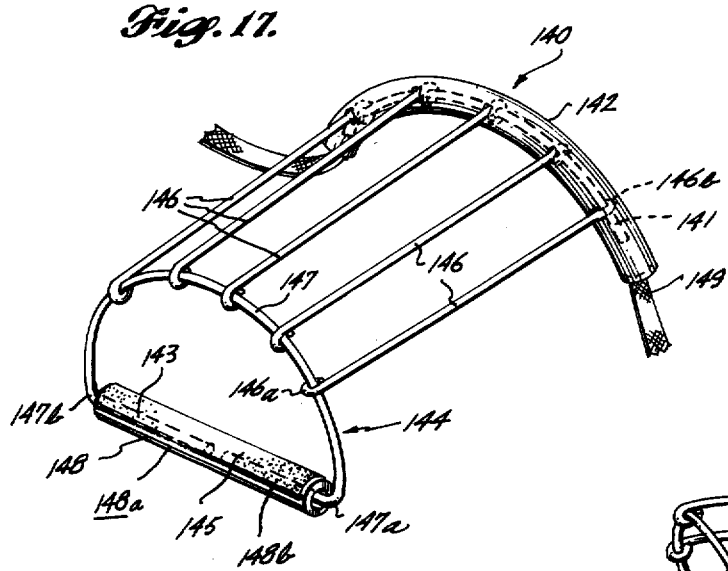
FIG. 17 is an isometric view showing another embodiment of the skin protective device of the present invention, adapted particularly for use on the hands and feet of a human user.
Figure 18:
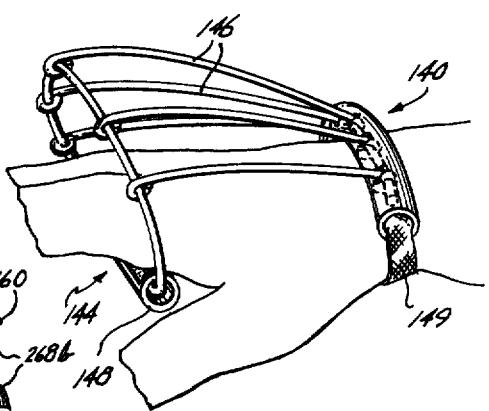
FIG. 18 is a elevational view showing the skin protective device of FIG. 17 in position on a human hand.

The protective devices as shown in FIGS. 17 and 18 are devices for specialized use on the hands or feet of a user, and are designed to permit a substantial amount of movement of the hands and feet without resulting contact between the protective element and the wounded area. In these embodiments the mounting pads take the form of a length of relatively stiff but bendable material, for instance, as shown in FIG. 17, plastic encased wire having approximately a ⅛ inch diameter with one mounting pad 140 comprising an arcuate length 141 of such wire fitted into a matching length of plastic or foam rubber tube 142.

The other mounting pad 144 defines a closed loop of plastic encased wire, which may take various outlines, depending upon application, including a circle, an elipse, or as shown in FIG. 17 a semi-circle length 147 with two straight line lengths 143 and 145 which extend directly toward each other from respective ends 147a and 147b of semi-circle length 147. Extending between mounting pad 140 and mounting pad 144 are a plurality of spaced protective elements 146 which are preferably also plastic encased wire of the same type as used in mounting pads 140 and 144. The protective elements 146 are individually joined to mounting pads 140 and 144 by crimping the respective ends 146a, 146b of each protective element 146 around arcuate length 141 and semi-circle length 147, to hold them in position. This arrangement permits relative movement between protective elements 146 and arcuate and semi-circle lengths 141, 147. Straight line lengths 143 and 145 of mounting pad 144 are preferably enclosed by a length of plastic tube or deformable foam rubber pad 148, which is sufficient in length to extend across the hand or foot of the user, with a portion of the outer surface 148a thereof being coated with an adhesive means 148b for adhering the length of tube 148, and hence mounting pad 144, to the sole of a foot or the palm of a hand.

Mounting pad 140 is secured to the wrist or ankle joint by adhesive tape 149 or other securing means such as shown in FIGS. 1–5. Tube 142 of mounting pad 140 preferably has a plurality of spaced slits defined therein to permit ends 146b of protective elements 146 access to arcuate length 141 positioned in tube 142, so that ends 146b may be crimped around arcuate length 141. Since the plastic encased wire used in mounting pads 140 and 144 and protective elements 146 is bendable, the configuration of mounting pads 140, 144 and protective elements 146 can be varied to suit individual applications. For instance, the configuration of protective elements 146 and mounting pads 140, 144 in FIG. 18 has been slightly altered from that shown in FIG. 17 to accommodate a wrist and hand application.

Referring now to FIGS. 19 and 20, another embodiment of a skin protective device adapted for use with a human foot is shown. A rectangular-shaped block 148 of foam rubber or similar material which is approximately 1 inch thick, and approximately the width of, and somewhat shorter than, the length of a foot, forms the base of the embodiment, with double-sided adhesive material strips 151 secured to the upper surface 150 thereof. The user's foot is positioned in the device as shown in FIG. 20 such that the sole of the foot comes into contact with adhesive material strips 151 on the upper surface 150 of the device, thereby assisting in securing the device to the foot of the user. A semicircular length 153 of wire, similar to the plastic encased wire used in the embodiment shown in FIGS. 17 and 18, extends substantially vertically from the opposing sides 152a and 152b of block 148 near the forward end 152 thereof, with straight sections of wire 154 and 155 extending from the respective ends 153a, 153b of semicircular length 153 into block 148, holding semicircular length 153 in place about the forward end 152 of block 148. The toes of the user are protected by a semicircular length 156 of plastic encased wire connected at the opposing ends 158 and 160 thereof to the semicircular length 153 at points along semicircular length 153 near upper surface 150 of block 148. Semicircular length 156 extends forwardly of block 148 substantially in the direction of its length and parallel with upper surface 151. A support length of wire 162 joins the midpoints 153a and 156a of semicircular lengths 153 and 156, extending outwardly from forward end 152 of block 148, and hence substantially over the toes of a user in the form of a quarter circle.

Two semicircular support elements 163 and 165 are provided which are adapted to fit around the ankle of the user and which provide the primary means for securing the device to the user's foot. Semicircular support elements 163 and 165 include semicircular wire sections 164 and 166, which are enclosed by plastic or foam rubber tubes 168 and 170. Extending from, and secured to, each of the ends 164a and 164b of semicircular wire portion 164 are strips of surgical tape or other securing means 167 and 169, which in use are positioned around the back of the user's ankle and secured thereto. Likewise, extending from, and secured to, ends 166a and 166b semicircular wire portion 166 are surgical tape strips 171 and 173 or other securing means which in use are positioned around the forward portion of the user's ankle and secured thereof. Longitudinal wire strips 168a, 168b and 168c, which are substantially rigid lengths of plasticencased wire, extend from spaced points along semicircular wire portion 164 to spaced points along semicircular length 153, thereby providing support for support element 163 and protection for the upper portion of the instep of the foot of the user. A different number of longitudinal wire strips may be conveniently used, depending on the application.

Additionally, extending between semicircular wire portion 166 and block 148 in the vicinity of the rear end 176 thereof are vertical wire strips 172a, 172b, 172c and 172d, similar in construction to longitudinal wire strips 168a, 168b and 168c. Vertical wire strips 172a and 172b extend from spaced points along semicircular wire portion 166 in the vicinity of one end 166b thereof into block 148 through openings defined in side 152a and are secured to an anchor element 173a embedded in block 148 near side 152a thereof. Vertical wire strips 172c and 172d extend between semicircular wire portion 166 in the vicinity of end 166a thereof to anchor element 173b embedded in block 148 near side 152b thereof and near end 176 thereof. Vertical wire strips 172a, 172b, 172c and 172d provide protection for the rear portion, including the heel, of the user's foot.

Referring now to FIGS. 21 and 22, an embodiment of the skin protective device of the present invention is shown which is specifically adapted for protection of skin wounds which extend around or in the area of a joint, such as a knee, while permitting movement of the joint. The skin protective device of FIGS. 21 and 22 comprises two elongated mounting pads 178 and 180 preferably made from a resilient, deformable material such as foam rubber. Mounting pads 178 and 180 have a substantially identical outline to that of the mounting pads of FIG. 1, although they are typically substantially longer, on the order of 10 to 36 inches long, depending upon the length required to extend around the joint and the wound area. Defined within each mounting pad 178 and 180 and running lengthwise thereof, is a series of rectangular-shaped cavities 182, each cavity in the embodiment shown in FIGS. 21 and 22 being approximately 1 inch long, and having a cross-sectional area large enough to receive lengths 183 of rigid material having approximately a ¼ inch diameter. Adjacent cavities are spaced apart approximately ¼ to ½ inch.

Communicating with each of the cavities 182 in each mounting pad 178 and 180 are openings 188, which extend from the respective upper surfaces 184 and 186 of mounting pads 178 and 180 to cavities 182. Openings 188 are large enough to permit ⅛ inch diameter plastic encased wire to feed through to cavities 182. As described above, lengths 183 of rigid material are positioned in each cavity 182. Extending between each length 183 positioned in cavities 182 of mounting pad 178 and corresponding lengths 183 positioned in corresponding cavities 182 in mounting pad 180 are a plurality of protective elements 190, in the form of semicircular lengths of plastic encased bendable wire or other substantially rigid non-resilient but bendable material. Ends 190a, 190b of each protective element 190 are bent outwardly and upwardly to form a U-shaped end portion which is insertable through openings 188 in mounting pads 178 and 180, and adapted to be hooked around lengths 183 positioned in cavities 182 of each mounting pad.

In use, mounting pads 178 and 180 are secured at their respective inner surfaces 192 and 194 to the opposite sides of the joint, such as the knee, shown in FIG. 22. The means for securing the mounting pads 178, 180 around the joint will vary depending upon application, and may conveniently take any of the forms of FIGS. 1–5. The protective elements 190, which extend between lengths 183 provide stand-off protection for a skin wound in that area, while permitting maximum freedom of natural movement of the joint. Lengths 183, positioned in cavities 182, provide the anchoring for the protective elements 190, while at the same time permit mounting pads 178 and 180 to flex sufficiently that they can be deformed to engage opposite sides of a joint. Such a configuration permits extensive movement of the joint without impairing the protective qualities of the device and without impairing its attachment about the joint.

Referring now to FIGS. 23 and 24, a variation on the embodiment of FIGS. 21 and 22 is shown. In the embodiment shown in FIGS. 23 and 24, a plurality of rigid support elements 200 are arranged successively within resilient, deformable plastic tubes 202 and 204, forming mounting pads 203 and 205, which replace mounting pads 78 and 80 in the embodiment shown in FIGS. 21 and 22. The configuration of protective elements 206 of the embodiment of FIGS. 23 and 24 is substantially identical to that of protective elements 190 of FIGs. 21 and 22, in that they are substantially semicircular in shape, with opposite ends 207, 208 of each protective element 206 formed into U-shaped end portions, which engage associated support elements 200 in each mounting pad 203, 205. Tubes 202 and 204 are made from a material which is sufficiently flexible that tubes 202 and 204 may be secured around a joint. The embodiment of FIGS. 23 and 24 include a pluralicy of adhesive strips 207 which secure mounting pads 203 and 205 in the correct position on the user. Other securing means, such as disclosed in FIGS. 2–5 may be substituted for the adhesive strips 207. Although the embodiment shown in FIGS. 23 and 24 is used for substantially the same purpose as the embodiment of FIGS. 21 and 22, one or the other embodiment may be more desirable depending on the particular application.

FIGS. 25 and 26 show a skin protective device which is adjustable in size, and which makes use of a material having special thermal properties known in the art generically as thermoplastic for the protector means of the device. Thermoplastic is a synthetic material which at elevated temperatures is pliable, and which can hence be molded to a desired shape, at which point the material is cooled, which results in its hardening to a rigid/semi-rigid state in the desired shape. Various thermoplastics are available which become pliable at differing temperatures. For use with the present invention, however, a lower temperature thermoplastic, e.g. 160°–185°, is preferred. These lower temperatures permit a more convenient working of the material in hospitals, etc. The use of thermoplastic has the advantage of permitting the physician to conveniently adjust the shape of and length of the protective elements to conform to the shape and size of the individual patient's body in the vicinity of the skin wound, as well as the size of the wound. This feature is particularly useful around joints, for instance the knee, as shown in FIG. 26. Referring to FIGS. 25 and 26 a typical embodiment using thermoplastic includes two elongated strips of foam rubber forming mounting pads 220 and 222, each mounting pad 220, 222 having defined therethrough from exterior side to interior side a plurality of slits 224 at spaced points therealong. Protector means 226 takes the form of strips of thermoplastic, which may be conveniently inserted through the slits 224 in the mounting pads 220 and 222.

More specifically, mounting pads 220 and 222, in the embodiment shown in FIGS. 25 and 26 have a cross-sectional dimension of 1 inch by 1 inch, and have a length which will vary from a few inches to over 3 feet, depending upon application. The thermoplastic strips forming the protector means 226 of the skin protective device may be, for example, approximately ½ inch wide, approximately 18 inches long and approximately ⅛ inch thick. These dimensions may of course vary, depending upon application. The thermoplastic strips initially are positioned between mounting pads 220 and 222, extending through mounting pads 220 and 222 at spaced points therealong and are then secured in position thereabout. As an example, thermoplastic strip 227, which forms a portion of protector means 226, is heat treated in the vicinity of one end portion 230 thereof, to enable end portion 230 to be deformed to fit around a portion of one mounting pad 222. End portion 230 of thermoplastic strip 227 is deformed so that it lays over top surface 232 of mounting pad 222, then bends downwardly at a right angle to conform to the exterior side 234 of mounting pad 222, then bent at another right angle through one slit 224 defined in mounting pad 222. At this point, the remainder of end portion 230 of thermoplastic strip 227 is bent upwardly at right angles against inner side 238 of mounting pad 232 and toward the undersurface 239a of that portion 239 of thermoplastic strip 227 which lies between mounting pads 220 and 222. End portion 230 is then bent at another right angle in the direction of the other mounting pad 220, thus lying parallel to the undersurface 239a of thermoplastic strip 227. In this position, end portion 230 and mating undersurface 239a are reheated to enable bonding of the two surfaces. This process is repeated for each thermoplastic strip forming protector means 226.

Initially the other end portion 240 of each thermoplastic strip, e.g. thermoplastic strip 227, is left completely straight and extends through the spaced slits 224 defined in mounting pad 220. In use, the position of mounting pad 220 relatively along the length of the thermoplastic strips is first determined in accordance with the size of the skin wound area. End portion 240, which is at the opposite end of each thermoplastic strip from end portion 230 is then heated, bent and secured to mounting pad 220 in a like configuration as end portion 230 is secured around mounting pad 227. If the skin wound area is relatively flat, such as on the chest, the back, the top of the foot, or the back of the hand, the thermoplastic strips will typically extend directly between the two mounting pads 220 and 222, parallel with the skin wound area as is shown in FIG. 25. If the skin wound area is on a contoured portion of the body, however, such as a leg, the thermoplastic strips will then be heated, bowed or bent accordingly, then cooled to set, to produce configurations such as shown in FIG. 26. Additional strength and rigidity for that portion of the thermoplastic strips between the mounting pads may be secured by rolling or folding that portion of the strips after heating.

After the skin protective device of FIGS. 25 and 26 has been sized for the wound, end portions 240 of the thermoplastic strips forming protector means 226 still extend out from mounting pad 220. End portions 240 are heated sufficiently to enable mounting pad 220 to be rotated in a clockwise direction 180°, such that end portions 240 of the thermoplastic strips now extend in the direction of mounting pad 222, with, for example, thermoplastic strip 227 lying flat across top surface 274 and a portion of exterior surface 246 of mounting pad 220. End portion 240 is then bent upwardly toward thermoplastic strip 227, conforming to the interior surface 248 of mounting pad 220 until end portion 240 intersects thermoplastic strip 227 at the undersurface 239a thereof, at which point it is reheated and bent for bonding to the undersurface 239a in the direction of mounting pad 222. Mounting pads 220 and 222 are then ready to be secured to the body by means shown in FIGS. 1–5.

Additionally, thermoplastic strips may be used with considerable success in several of the other embodiments, particularly as an alternative to the plastic encased wire of, for instance, the embodiments of FIGS. 17–21.

Figure 27:
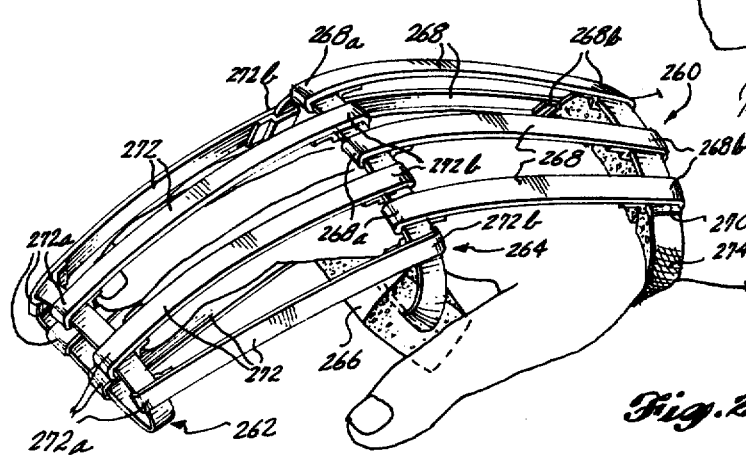
FIG. 27 is an isometric view showing another embodiment of the skin protective device of the present invention, adapted particularly for use on the hands of a user.

Referring now to FIG. 27, a variation of a skin protective device using theromplastic and adapted particularly for the hand is shown. It is similar in many respects to the embodiments shown in FIGS. 15 through 18, with mounting pad 260 being resiliently deformable, similar to mounting pad 136 of the embodiment of FIGS. 15 and 16. A substantially oval-shaped, closed loop made from a strip of thermoplastic forms a second mounting pad 262, and another substantially oval, nearly closed loop forms mounting pad 264 which is positioned between mounting pads 260 and 262. Positioned around a portion of mounting pad 264 is an elongated block 266 of resilient material such as foam rubber, a lengthwise portion of the circumferential surface of which has an adhesive secured thereto. Extending between mounting pads 260 and 264 at spaced points therealong are a first plurality of thermoplastic strips 268. One end 268a of each thermoplastic strip is bonded to mounting pad 264, while the other end 268b thereof is fitted through slits 270 in mounting pad 260 and bonded back upon itself, similar to that of the embodiment of FIG. 26. Extending between mounting pads 262 and 264 are a second plurality of thermoplastic strips 272. One end 272a of each thermoplastic strip 272 is bonded to mounting pad 262, while the other end 272b is bonded to mounting pad 264 at spaced point therealong intermediate successive thermoplastic strips 268. In use, mounting pad 260 is secured about the upper portion of the wrist by adhesive strips 274 or other suitable securing means, and the hand of the user is inserted through the loop formed by mounting pad 264, such that pad 266 fits against the palm of the hand, and such that mounting pad 262 is positioned just beyond the ends of the fingers of the hand. Thermoplastic strips 268 and 272 then lay over and are spaced away from the back of the hand and fingers.

Thus, a new protective skin device has been disclosed, which has the capability of protecting a skin wound area from contact with foreign articles, and at the same time permitting air to freely circulate about the skin wound area and permitting blood to freely flow to the skin wound area. Several embodiments of the invention have also been disclosed which are specially adapted for protection of particular body areas, such as around the joints, the hands and the feet.

It should be understood that certain changes in the details and the materials of the embodiments disclosed can be made without departing from the spirit of the invention. For instance, various materials may be used successfully for the protector means, and various means can be utilized to attach the protector means to the mounting pads, including means permitting the protector means to be removable, such as shown in FIG. 28. It should also be understood that the devices can be used with equal facility on animals as well as humans. Furthermore, although all of the embodiments have disclosed plural mounting means, it should be understood that a single mounting pad, taking various configurations, for instance a circle, a rectangle or virtually any other geometric shape, may be used. Furthermore, the arrangement of parts and the description of the materials used in the invention, which have been described and illustrated in order to explain the nature of the invention may be changed by those skilled in the art within the spirit of the invention as expressed in the claims which follow.

What is claimed is:

1. An article for protecting a first skin area on the body from foreign contact, while permitting air to circulate thereabout, comprising:
   a. resiliently deformable mounting means positionable on, and conformable to the contour of, substantially any portion of the body including a second skin area situated relatively near said first skin area;
   b. means for 1) securing said mounting means to said second skin area without producing residual pressure thereon, such that the blood supply to said first and second skin areas is substantially unaffected when said mounting means is so secured to said second skin area, and further for 2) maintaining said mounting means in position on, and in conformance to the contour of, said second skin area during substantially any normal movement of the one portion of the body which includes the location of said first skin area; and
   c. protector means capable of passing air between the atmosphere and said first skin area and mounted on said mounting means so as to extend over and be spaced away from said first skin area, said protector means having sufficient rigidity to substantially prevent foreign contact with said first skin area, wherein said resiliently deformable mounting means is of such a size and configuration and sufficiently compressible and wherein said protector means is mounted thereon in such a manner, that said mounting means is capable of absorbing external pressure exerted thereon, including pressure exerted by said protector means as a result of said normal movement of said one portion of the body, without the character of the contact between said mounting means and said second skin area being substantially altered, whereby the supply of blood into said first and second skin areas remains substantially unaffected.

2. An article of claim 1, wherein said protector is air permeable.

3. An article of claim 1, wherein said mounting means is a foam material.

4. An article of claim 1, including means for removably mounting said protector means on said mounting means.

5. An article of claim 1, including means for resiliently mounting said protector means on said mounting means.

6. An article of claim 1, wherein said mounting means includes two mounting pads positionable on opposite sides of said first skin area, said protector means being mounted on, and extending between, said two mounting pads and over said first skin area.

7. An article of claim 6, wherein each of said mounting pads has an upper surface, an opposed undersurface, and two opposed side surfaces, said undersurface lying adjacent said second skin area in use, and wherein each of said mounting pads includes at least one notch defined in said undersurface thereof.

8. An article of claim 7, wherein said notch in each of said mounting pads extends between said opposed side surfaces thereof and is substantially V-shaped in outline, said notch having sides which converge in the direction of said upper surface of said mounting pad.

9. An article of claim 1, wherein said securing and maintaining means is permanently affixed to said mounting means.

10. An article of claim 1, including means for releasably securing said securing and maintaining means to said mounting means.

11. An article of claim 6, wherein each of said mounting pads includes an upper surface, a lower surface, and two end surfaces therebetween, each of said two end surfaces having an inclined portion extending outwardly from said upper surface toward said lower surface, and a blunt portion extending upward from said lower surface to intersect with said inclined portion, said blunt portion having an angle to the vertical substantially less than that of said inclined portion.

12. An article of claim 1, wherein said protector means includes a plurality of parallel, spaced bars.

13. An article of claim 12, wherein said mounting means has defined therein a plurality of grooves to receive a portion of said bars.

14. An article of claim 1, wherein said protector means includes a single bar.

15. An article of claim 14, wherein said bar has two ends, and wherein said mounting means has defined therein grooves to receive said two ends.

16. An article of claim 1, wherein said protector means includes a sheet of air permeable material.

17. An article of claim 1, wherein said protector means includes a material sheet having a plurality of openings defined therein.

18. An article of claim 1, wherein said protector means includes a plurality of strips of a thermoplastic material.

19. An article of claim 1, wherein said protector means includes a plurality of strips of rigid material, each of said strips being rotatably mounted on said mounting means, and rotatably connected to certain other of said strips to form a scissors-like grid.

20. An article of claim 1, wherein said securing and maintaining means includes at least one adhesive tape strip, at least one portion of said adhesive tape strip being secured to said mounting means, the remainder of said adhesive tape strip being adapted to be attached to the skin of a user.

21. An article of claim 1, wherein said securing and maintaining means includes an adhesive applied to one surface of said mounting means, said one surface being positioned against and adhering to said second skin area in use.

22. An article of claim 1, wherein said securing and maintaining means includes at least one band of material positionable about the body of a user in said second skin area, and further includes means for removably securing said mounting means to said band.

23. An article of claim 22, wherein said removably securing means includes first adhering means attached to said band and second adhering means attached to said mounting means, said first and second adhering means being releasably mateable with each other.

24. An article of claim 23, wherein said band has two ends, at least one end of which has attached thereto said first adhering means.

25. An article of claim 24, including means permanently securing the other end of said band to said mounting means.

26. An article of claim 24, wherein said first adhering means has two portions thereof, one portion being attached to said band in the vicinity of said one end thereof, the other portion being attached to said band in the vicinity of the other end thereof.

27. An article of claim 1, wherein said mounting means includes an upper surface, and an opposed undersurface, said undersurface lying adjacent said second skin area in use, and wherein said article further includes a substantially nondeformable support means positioned in said mounting means between said undersurface thereof and a point on said mounting means where said protector means is mounted on said mounting means, such that contact between said protector means and said first skin area is prevented.

28. An article of claim 27, wherein said nondeformable support means includes a series of spaced lengths of nondeformable material positioned in said mounting means substantially along the length thereof.

29. An article of claim 27, wherein said article further includes a series of spaced lengths of nondeformable material positioned in a tubelike element of flexible material, and wherein said protector means includes a plurality of parallel, spaced bars, one of said lengths of nondeformable material being positioned in said tubelike element between each of said bars and said undersurface of said mounting means.

30. An article of claim 6, wherein the depth of one mounting pad is greater than the depth of the other mounting pad.

31. An article of claim 30, wherein the depth of said one mounting pad is approximately twice as great as the depth of said other mounting pad.

32. An article of claim 6, including a plurality of spaced anchor elements positioned, respectively, in each of said mounting pads along the length thereof, and wherein said protector means extends between said anchor elements in said mounting pads.

33. An article of claim 32, wherein said protector means includes a plurality of lengths of a rigid, yieldable material, each of said lengths extending between one of said anchor elements in each of said mounting pads, and wherein each of said lengths includes attaching means at each end thereof for securing said lengths to said anchor elements.

34. An article of claim 33, wherein said attaching means includes U-shaped end portions of said lengths, said U-shaped end portions being configured to hook around and be secured to said anchor elements.

35. An article for protecting a first skin area from a contact thereof while letting air circulate thereabout, comprising:
 a. first and second mounting means positionable on second and third skin area situated relatively near and on opposite sides of said first skin area, said first mounting means defining substantially a closed loop;
 b. first means for securing a portion of said first mounting means to said second skin area in the vicinity of the palm of a user's hand, the remainder of said first mounting means being raised off of, and substantially encircling the user's hand;
 c. second means for securing said second mounting means to said third skin area in the vicinity of the user's wrist;
 d. protector means attached between said first and second mounting means, such that said protector means extends over and is spaced away from said first skin area; and,
 e. means attaching said protector means to said second mounting means, and to the remainder of said first mounting means.

36. An article of claim 35, wherein said portion of first mounting means includes an elongated support element having two ends, and a relatively rigid length of material in the form of a loop which extends into said two ends, said support means being adapted to fit across the palm of the users's hand, the fingers of the user's hand extending through said loop formed by said length when said support element is adhered to the palm of the user's hand.

37. An article of claim 35 including a third substantially rigid mounting means which takes the form of a closed loop, said first mounting means being positioned intermediate said second mounting means and said third mounting means, and rigid protector means extending between and secured to said first mounting means and said third mounting means.

38. An article of claim 35, wherein said protector means includes strips of thermoplastic material.

39. An article for protecting a first skin area from a contact thereof while letting air circulate thereabout, comprising:
 a. first mounting means sufficient in size to support a human foot thereon;
 b. second mounting means configured so as to fit about the ankle of a user;
 c. first means for securing said first mounting means to the sole of the foot of the user;
 d. second means for securing said second mounting means to said ankle;
 e. a plurality of strips of substantially rigid, material extending between and secured to said first and second mounting means so as to prevent a contact thereof; and
 f. means for attaching said strips to said first and second mounting means.

40. An article of claim 39, wherein said first means includes sections of double-backed adhesive tape.

41. An article of claim 39, wherein said rigid material is a thermoplastic material.

42. An article of claim 39 wherein said first mounting means has forward and rear ends, and wherein said plurality of strips includes a first strip secured at opposite ends to said first mounting means and defining a substantially vertical loop in the vicinity of said forward end of said first mounting means, said loop being sufficient in size to permit insertion of the toes of a foot of the user therethrough; a second strip secured at opposite ends thereof to said first stip and defining a substantially horizontal semicircle fowardly from said first strip; at least a third strip extending between and secured to said first strip and said second mounting means, and at least fourth and fifth strips extending between and secured to said second mounting means and said first mounting means in the vicinity of said rear end thereof.

43. An article of claim 6, wherein said protector means includes means permitting relative movement between said mounting pads when said mounting pads are not operatively positioned on the body, so that the area between said mounting pads is adjustable in accordance with the size and shape of said first skin area.

44. An article of claim 6, wherein said protector means includes a plurality of strips of thermoplastic material, which extend between said mounting pads when the article is operatively positioned on the body.

45. An article of claim 44, wherein said securing and maintaining means includes first strip-like means securely affixed to the body on opposite sides of said first skin area, and further including second strip-like means securely affixed to each of said mounting pads, said first and second strip-like means being releasably mateable with each other.

* * * * *